United States Patent [19]
Kaida et al.

[11] Patent Number: 4,901,733
[45] Date of Patent: Feb. 20, 1990

[54] PULSE WAVE DETECTING APPARATUS

[75] Inventors: Noriyuki Kaida, Kakamigahara; Hifumi Yokoe, Kosai; Chikao Harada; Minoru Niwa, both of Nagoya; Masanobu Yasui, Kyoto, all of Japan

[73] Assignee: Colin Electronics Co., Ltd., Aichi, Japan

[21] Appl. No.: 312,178

[22] Filed: Feb. 21, 1989

[30] Foreign Application Priority Data

Feb. 23, 1988 [JP] Japan .................. 63-22490[U]

[51] Int. Cl.$^4$ .................................................. A61B 5/02
[52] U.S. Cl. .................................... 128/687; 128/672; 128/690
[58] Field of Search .................... 128/670–672, 128/677–683, 687–690, 644, 686

[56] References Cited

U.S. PATENT DOCUMENTS

| | | | |
|---|---|---|---|
| 3,299,882 | 1/1967 | Masino | 128/687 |
| 4,185,621 | 1/1980 | Morrow | 128/672 |
| 4,307,727 | 12/1981 | Haynes | 128/672 |
| 4,784,152 | 11/1988 | Shinoda et al. | 128/690 |
| 4,802,488 | 2/1989 | Eckerle | 128/672 |

FOREIGN PATENT DOCUMENTS 3030566  3/1982  Fed. Rep. of Germany ...... 128/672

Primary Examiner—Angela D. Sykes
Attorney, Agent, or Firm—Oliff & Berridge

[57] ABSTRACT

A pulse wave detecting apparatus having a pulse wave sensor for detecting pulse wave produced from an arterial vessel of a subject, the pulse wave sensor being movable along a cross line crossing the arterial vessel so as to be positioned in place relative to the arterial vessel, and pressed against a body surface of the subject so as to detect the pulse wave produced from the arterial vessel, a frame member for being set on the body surface of the subject, a guide device supported by the frame member, for guiding the pulse wave sensor within a predetermined length along the cross line, a feeding screw supported by the frame member such that the feeding screw is rotatable about a longitudinal axis thereof parallel to the cross line, the feeding screw being threadedly engaged with the pulse wave sensor, a drive motor supported by the frame member such that the drive motor is located adjacent to the body surface when the frame member is set on the body surface of the subject, and a transmission device provided between the drive motor and the feeding screw, for transmitting rotating force of the drive motor to the feeding screw, so as to move the pulse wave sensor along the cross line.

6 Claims, 2 Drawing Sheets

PULSE WAVE DETECTING APPARATUS

BACKGROUND OF THE INVENTION

1. Field of the Invention

The present invention relates to an apparatus for detecting pulse wave produced from an arterial vessel of a living body.

2. Related Art Statement

The Assignee to which the present application is assigned, previously filed Japanese patent application No. 62-109594 on May 2, 1987 and Japanese Utility Model Application No. 62-178067 on Nov. 20, 1987 in each of which they disclosed a device having a sensor for detecting pulse wave produced from an artery of a subject, the sensor being movable along a cross line crossing the artery so as to be positioned in place relative to the artery, and pressed against a body surface over the artery so as to detect the pulse wave. Each of the devices also has a pair of air-tight chambers formed of bellows or rubber bags, on both sides of the pulse wave sensor, and the pulse wave sensor is moved along the cross line as a result that pressure level in each of the pair of chambers are varied.

The above-indicated pulse wave detecting devices, however, suffer from a problem that, even after the pulse wave sensor has been positioned in place, the sensor may be moved due to changed pressure difference between the pressure levels of the pair of air-tight chambers resulting from, for example, failure of electric power applied to the device or leakage of air from one of the chambers.

The above Japanese patent application No. 62-109594 further teaches that the pulse wave sensor may be moved by means of a feeding screw rotated by a drive motor. This arrangement assures that the sensor is retained in place. However, if the drive motor is located spaced apart from the body surface of the subject via the pulse wave sensor disposed therebetween, an overall height of the pulse wave detecting device would be disadvantageously increased. Japanese patent application No. 62-109594 was laid-open under Publication No. 63-275320 on Nov. 14. 1988.

SUMMARY OF THE INVENTION

It is therefore an object of the present invention to provide a pulse wave detecting apparatus which is capable of securely retaining the pulse wave sensor in place and has a comparatively small height.

The above object has been achieved by the present invention, which provides a pulse wave detecting apparatus comprising, (a) a pulse wave sensor for detecting pulse wave produced from an arterial vessel of a subject, the pulse wave sensor being movable along a cross line crossing the arterial vessel so as to be positioned in place relative to the arterial vessel, and pressed against a body surface of the subject so as to detect the pulse wave produced from the arterial vessel; (b) a frame member for being set on the body surface of the subject; (c) guide means supported by the frame member, for guiding the pulse wave sensor within a predetermined length along the cross line; (d) a feeding screw supported by the frame member such that the feeding screw is rotatable about a longitudinal axis thereof extending parallel to the cross line, the feeding screw being threadedly engaged with the pulse wave sensor; (e) a drive motor supported by the frame member such that the drive motor is disposed adjacent to the body surface when the frame member is set on the body surface of the subject; and (f) a transmission device provided between the drive motor and the feeding screw, for transmitting rotating force of the drive motor to the feeding screw, so as to move the pulse wave sensor along the cross line.

In the pulse wave detecting apparatus constructed as described above, the pulse wave sensor is moved along a cross line crossing an arterial vessel, while being guided by the guide means supported by the frame member, as a result that the feeding screw threadedly engaged with the sensor is rotated by the drive motor via the transmission device. Once the pulse wave sensor is accurately positioned relative to the arterial vessel, the sensor is advantageously prevented, due to the thread engagement with the feeding screw, from being moved in an axial direction of the feeding screw. Thus, the pulse wave sensor is securely retained in place.

Furthermore, in the present apparatus, the drive motor is supported by the frame member such that the motor is located adjacent to the body surface of the subject when the frame member is set on the body surface, and the power transmission device is provided between the drive motor and the feeding screw. Thus, the pulse wave sensor, drive motor and transmission device are supported by the frame member such that all of them are located along the body surface of the subject when the frame member is set on the surface. The present apparatus does not suffer from the problem of the increased height thereof due to the employment of the feeding screw, drive motor and transmission device.

In a preferred embodiment of the present invention, the apparatus further comprises detecting means for detecting that the pulse wave sensor has been moved along the cross line to a middle point of the predetermined length. In this case, the pulse wave sensor is movable over a sufficient length in opposite directions from the middle point, and accordingly the sensor is reliably positioned in place relative to the target arterial vessel.

In a preferred form of the above embodiment of the invention, the detecting means comprises a reflection plate mounted on the pulse wave sensor, and a photocoupler supported by the frame member, for emitting a light beam toward the reflection plate and detecting the light beam reflected by the reflection plate, the photocoupler generating electric signal if an intensity of the received light beam exceeds a reference value, the signal representing that the pulse wave sensor has been moved to the middle point of the predetermined length.

In another embodiment of the apparatus of the invention, the pulse wave sensor comprises a movable member including a threaded portion with which the feeding screw is threadedly engaged, a diaphragm supported by the movable member such that the diaphragm defines a fluid-tight space in the movable member, a presser member supported by the diaphragm such that the presser member is movable relative to the movable member in a direction substantially perpendicular to the body surface of the subject as pressure in the fluid-tight space is varied, and a pressure detector secured to the presser member, for detecting the pulse wave produced from the arterial vessel of the subject and generating electric signal representing the detected pulse wave, the pressure detector being pressed against the body surface when the presser member is moved toward the body surface.

In a further embodiment of the apparatus of the invention, the guide means comprises a pair of parallel guide rails supported by the frame member.

In yet another embodiment of the apparatus of the invention, the transmission device comprises a reduction-gear train consisting of a plurality of gears.

BRIEF DESCRIPTION OF THE DRAWINGS

The above and optional objects, features and advantages of the present invention will be better understood by reading the following detailed description of the presently preferred embodiment of the invention, when considered in conjunction with the accompanying drawings in which.

DETAILED DESCRIPTION OF THE PREFERRED EMBODIMENT

Figure 1:
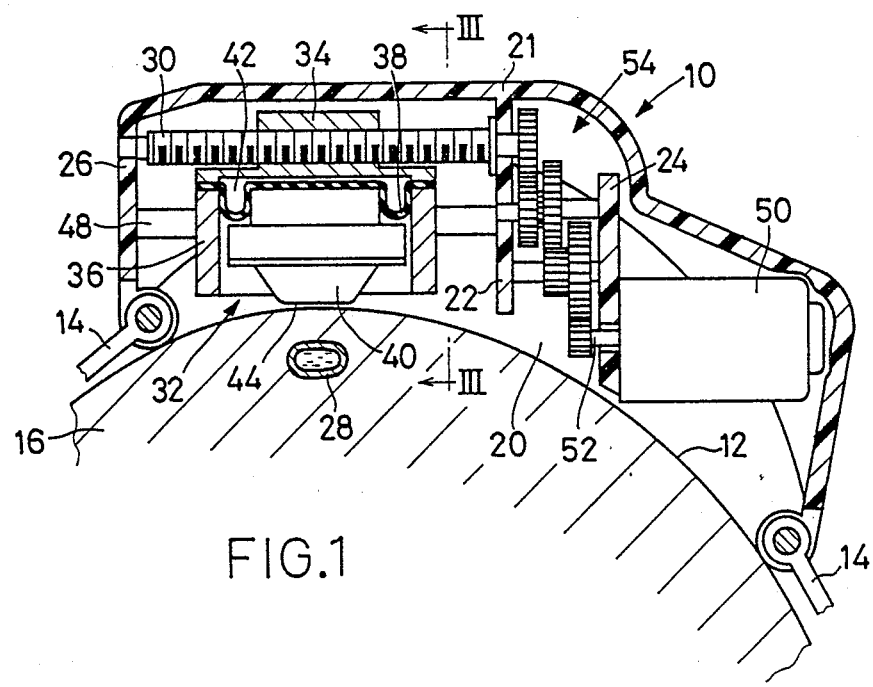
FIG. 1 is a cross-sectional view of a pulse wave detecting apparatus of the present invention set on a wrist of a subject.

A pulse wave detecting apparatus embodying the present invention is illustrated in FIGS. 1-4. In the figures, reference numeral 10 designates a housing having a single opening which is opposed to a body surface 12 of a wrist 16 of a subject when the housing 10 is set on the wrist 16. The housing 10 is detacheably set on the body surface 12 with the help of a band 14. In the present embodiment, the housing 10 serves as the frame member.

Figure 4:
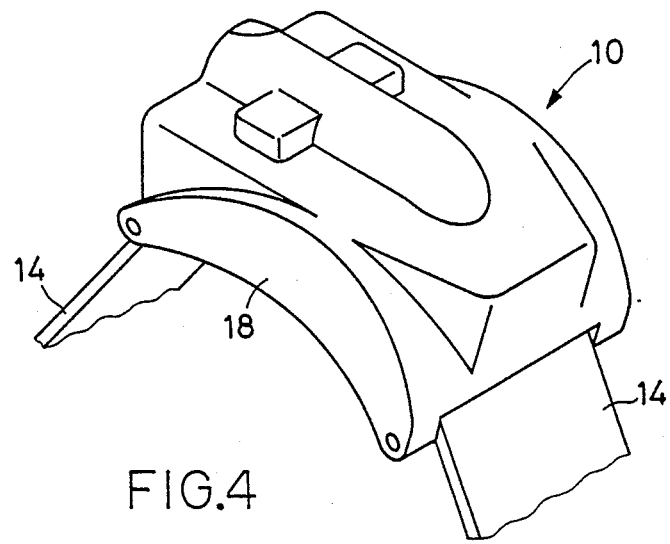
FIG. 4 is a reduced perspective view of the apparatus of FIG. 1.

As clearly shown in the perspective view of FIG. 4, the housing 10 has a pair of generally crescent-shaped longitudinal side walls 18, 20, and an outwardly protruded or swollen ceiling 21. The protruded portion extends longitudinally of the housing 10, and widely occupies a central portion of the ceiling 21. The housing 10 further has a first and a second plate-like support portion 22, 24 at longitudinally intermediate locations thereof. The first and second support portions 22, 24 extend parallel to each other, and each are connected at opposite ends thereof to the pair of longitudinal side walls 18, 20. A feeding screw 30 is supported at opposite ends thereof by the first support portion 22 and a left-hand sidewall 26 (FIG. 1) opposed to the first support portion 22, such that the screw 30 is rotatable about a longitudinal axis thereof. The feeding screw 30 extends longitudinally of the housing 10 at a middle location between the pair of longitudinal side walls 18, 20 near the ceiling 21. When the housing 10 is set on the body surface 12, the longitudinal axis of the feeding screw 30 crosses over a radial artery 28. A pulse wave sensor 32 is threadedly engaged with the feeding screw 30. In the present embodiment, the radial artery 28 corresponds to the arterial vessel from which the present apparatus pulse wave sensor 32 detects pulse wave.

The pulse wave sensor 32 includes a rectangular casing 36, a diaphragm 38 and a presser member 40. The casing 36 has a threaded portion 34 protruding from a central portion of an upper surface thereof (FIG. 1). The pulse sensor 32 is threadedly engaged with the feeding screw 30 at the threaded portion 34. The diaphragm 38 is supported by the casing 36 such that the diaphragm 38 defines an air-tight space 42 in the casing 36. The presser member 40 is supported by the diaphragm 38 such that the presser member 40 is movable relative to the casing 36 in a direction perpendicular to the body surface 12. Thus, the presser member 40 is advanced out of the casing 36 and retracted into the casing 36. The air-tight space 42 is supplied with pressurized fluid such as pressurized air from a fluid supplying device (not shown). Upon expansion of the diaphragm 38 due to the pressurized fluid supplied to the air-tight space 42, the presser member 40 is moved relative to the casing 36, and pressed against the body surface 12 with a pressing force corresponding to pressure level in the space 42. A pressure detector such as a pressure-sensitive diode (not shown) is secured to a pressing surface 44 of the presser member 40. The pressure detector detects pulse wave, that is, pressure oscillation transmitted thereto from the radial artery 28 via the body surface 12, and generates pulse wave signal representing the detected pulse wave to a control device (not shown).

Figure 3:
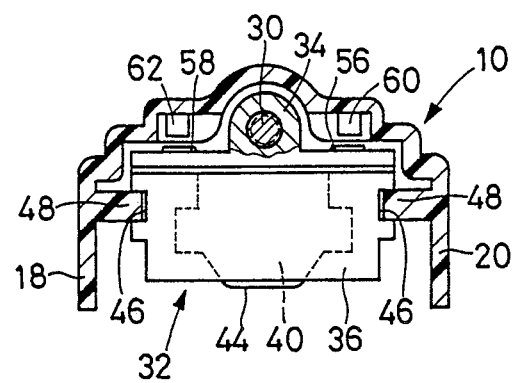
FIG. 3 is a cross sectional view taken along line III—III of FIG. 1, partly showing the apparatus of FIG. 1.

As clearly shown in FIG. 3, the rectangular casing 36 has a pair of guide grooves 46, 46 in opposite side walls extending parallel to the axis of the feeding screw 30. Meanwhile, the longitudinal side walls 18, 20 have at inner surfaces thereof a pair of guide rails 48, 48 between the first support portion 22 and the opposed side wall 26. The pulse wave sensor 32 (casing 36) is movable within a predetermined permitted length in a direction substantially perpendicular to the radial artery 28, such that the casing 36 is slid or guided on the pair of guide rails 48, 48 with the guide grooves 46, 46 thereof fitted on the rails 48, 48. In the present embodiment, the guide rails 48, 48 serve as the guide means for guiding the pulse wave sensor along the cross line crossing the arterial vessel.

Figure 2:
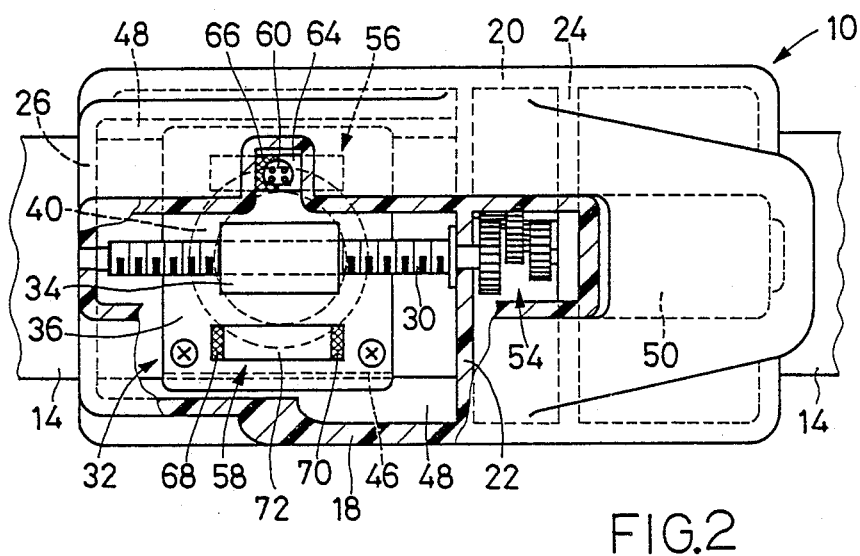
FIG. 2 is a plan view of the apparatus of FIG. 1, with a part thereof removed.

Referring back to FIG. 1, a drive motor 50 is supported by the second support portion 24 such that the drive motor 50 is located near the body surface 12 and spaced apart a predetermined distance from the pulse wave sensor 32 along the body surface 12. A reduction-gear train 54 consisting of a plurality of gears is provided between the first and second support portion 22, 24. Specifically, the gear train 54 operatively connects between an output shaft 52 of the drive motor 50 and a right-hand end of the feeding screw 30 (FIGS. 1 and 2). Thus, rotating force of the drive motor 50 is transmitted to the feeding screw 30 via the reduction gear train 54. In the present embodiment, the reduction gear train 54 serves as the transmission device.

A first and a second elongate reflection plates 56, 58 are fixed to the upper surface of the casing 36 (FIG. 1) on both sides of the threaded portion 34, each in a parallel relationship with the feeding screw 30. Meanwhile, a first and a second photocouplers 60, 62 are secured to the inner surface of the ceiling 21 of the housing 10, such that the first and second photocouplers 60, 62 are aligned with the first and second reflection plates 56, 58, respectively, as viewed longitudinally of the housing 10, and located at a longitudinally middle location between the first support portion 22 and the opposed side wall 26 (or a middle location of the length of the guide rails 48, 48). In FIG. 2, the second photocoupler 62 is not illustrated. Each of the photocouplers 60, 62 emit a light beam toward the upper surface of the pulse wave sensor 32 (casing 36), and detecting the reflected light beam therefrom. If an intensity of the detected light beam is higher than a reference value, each photocoupler 60, 62 generates detection signal representing detection of the intense light beam, to the previously-indicated control device.

The first reflection plate 56 includes a reflection portion 64, and a non-reflection portion 66 bounded by the reflection portion 64 at a longitudinally middle position of the plate 56. The second reflection plate 58 includes a pair of small non-reflection portions 68, 70 at opposite ends thereof and a large reflection portion 72 between the non-reflection portions 68, 70. Upon reception of the light beams reflected by the reflection portions 64, 72 of the first and second reflection plates 56, 58, the respective first and second photocouplers 60, 62 generate the above-described reflection signal to the control device. Thanks to the first reflection plate 56 and the first photocoupler 60 it is possible to judge to which side the pulse wave sensor 32 is currently deviated from a middle point of the predetermined permitted length within which the sensor 32 is permitted to be moved relative to the housing 10, because the line separating the reflection and non-reflection portions 64, 66 from each other corresponds to the middle point of the permitted length. Meanwhile, it is possible to regulate an amount of movement of the pulse wave sensor 32 in each of the opposite directions, by utilizing the first and second reflection plates 56, 58 and the first and second photocouplers 60, 62.

There will be described the operation of the pulse wave detecting apparatus constructed as described above, for detecting the pulse wave produced from the radial artery 28.

Upon application of electric power to the control device (not shown) to which the housing 10 is connected via electric wiring or the like, the pulse wave sensor 32 is accurately positioned at the middle point of the above-described predetermined permitted length. If the first photocoupler 60 generates detection signal to the control device in the case where the reflection portion 64 of the first reflection plate 56 is located on a thumb side of the body surface 12 (or wrist 16) and accordingly the non-reflection portion 66 of the same 56 is located on a little-finger side, it is judged that the pulse wave sensor 32 is deviated to the thumb side. Consequently, the sensor 32 is moved to the little-finger side as a result that the feeding screw 30 is rotated by the drive motor 50 activated. If the first photocoupler 60 ceases generating detection signal, the drive motor 50 is stopped and the sensor 32 is positioned at the target middle point of the permitted length and retained thereat. In the present embodiment, the first reflection plate 56 and the first photocoupler 60 serve as the detecting means for detecting that the pulse wave sensor has been moved to the middle point of the permitted length.

With the pulse wave sensor 32 retained at the middle point of the permitted length, the housing 10 is set on the body surface 12 such that the presser member 40 is positioned generally above the radial artery 28. Upon operation of an activation switch provided on the control device, the air-tight space 42 is supplied with pressurized air from the supplying device and the pressure detector secured to the pressing surface 44 of the presser member 40 is pressed against the body surface 12. The pressure level in the air-tight space 42 is controlled so that the amplitude of pulse wave signal supplied from the pressure detector is increased to a maximum. The pulse wave sensor 32 is moved, as needed, by the feeding screw 30, so as to be accurately positioned relative to the radial artery 28, namely, right above the artery 28. It is recommended that it be judged whether or not the pulse wave sensor 32 is retained in place right above the radial artery 28 at regular intervals of time or each time a predetermined number of pulses of the pulse wave have been detected, and that, if the judgement is negative, the sensor 32 is automatically re-positioned right above the artery 28 as described above. Even in the case where the pulse wave sensor 32 (housing 10) is moved relative to the radial artery 28 during the detection of the pulse wave due to, for example, physical motion of the subject, the present apparatus is capable of accurately detecting pulse wave.

As is apparent from the foregoing description, in the present pulse wave detecting apparatus, the pulse wave sensor 32 is threadedly engaged with the feeding screw 30 through the threaded portion 34 thereof, and the feeding screw 30 is rotated by the drive motor 50 via the reduction-gear train 54. Once the pulse wave sensor 32 is positioned at the middle point of the predetermined permitted length, or once the sensor 32 is positioned right above the radial artery 28, the sensor 32 is advantageously prevented, due to the thread engagement with the feeding screw 30 from being moved along the axis of the feeding screw 30. Thus, the pulse wave sensor 32 is securely retained relative to the radial artery 28. Also, the pulse wave sensor 32 positioned at the middle point of the predetermined permitted length is prevented from being moved therefrom, for example when the housing 10 is set on the wrist 16.

Furthermore, in the present apparatus, the drive motor 50 is accommodated in the housing 10 such that the motor 50 is spaced apart a predetermined distance from the pulse wave sensor 32 along the body surface 12, and the reduction gear train 54 is provided between one end of the feeding screw 30 and the drive motor 50. Thus, the pulse wave sensor 32, drive motor 50 and reduction-gear train 54 are located adjacent to the body surface 12 when the housing 10 is set on the wrist 16. Consequently, the employment of the drive motor 50, feeding screw 30 and reduction-gear train 54, does not lead to increasing the dimension of height of the overall apparatus (overall housing 10).

Moreover, in the present apparatus, thanks to the first photocoupler 60 and the first reflection plate 56, the pulse wave sensor 32 is accurately positioned at the middle point of the predetermined permitted length within which the sensor 32 is permitted to be moved. Thus, the sensor 32 is movable over a sufficient length in each of the opposite directions, namely, to both the thumb and little-finger sides of the wrist 16. This arrangement contributes to reliably positioning the sensor 32 relative to the radial artery 28.

While in the illustrated embodiment an axis of the output shaft 52 of the drive motor 50 extends parallel to the axis of the feeding screw 30, it is possible to dispose the drive motor such that the axis of the output shaft of the drive motor is angled with respect to the axis of the feeding screw 30, so that the drive motor is positioned more suitably along a curvature of the body surface 12 when the apparatus (housing 10) is set on the wrist 16. In this case, the plurality of gears of the reduction-gear train 54, which transmits the rotating force of the drive motor to the feeding screw 30, may be replaced with a transmission device of a type including a flexible joint. Alternatively, the drive motor may be disposed such that the axis of the output shaft of the drive motor is normal to the axis of the feeding screw 30, and that the rotating force of the drive motor is transmitted to the feeding screw 30 via a transmission device of a type including a worm and a pinion.

While in the illustrated embodiment the pair of guide rails 48, 48 serving as the guide means are supported by the longitudinal side walls 18, 20 of the housing 10 and the pair of guide grooves 46, 46 in which the guide rails 48, 48 are slidably fitted are formed in the corresponding side walls of the casing 36 of the pulse wave sensor 32, it is possible to form a pair of guide grooves serving as the guide means, in the side walls 18, 20 of the housing 10, and provide a pair of guide rails on the corresponding sides walls of the casing 36 of the sensor 32. Alternatively, it is possible to use, as the guide means, the side walls 18, 20 of the housing 10, without providing the walls 18, 20 with any exclusive elements such as guide rails or guide grooves. In this case, the sensor 32 is slid directly on the side walls 18, 20.

Although in the illustrated embodiment the housing serving as the frame member has the single opening, it is possible to employ as the frame member a housing having one or more through-holes formed therethrough.

It is to be understood that the illustrated apparatus provides various advantages even in the case where none of the photocouplers 60, 62 or the reflection plates 56, 58 are employed.

While the illustrated apparatus is adapted to detect pulse wave produced from a radial artery, it is possible to apply the principle of the present invention to an apparatus adapted to detect pulse wave produced from other arteries such as a dorsal pedal artery.

While the present invention has been described in its presently preferred embodiment with detailed particularities, it is to be understood that the invention may be embodied with various changes, improvements and modifications that may occur to those skilled in the art without departing from the spirit and scope of the invention defined in the appended claims.

What is claimed is:

1. A pulse wave detecting apparatus comprising:
   a pulse wave sensor for detecting pulse wave produced from an arterial vessel of a subject, said pulse wave sensor being movable along a cross line crossing said arterial vessel so as to be positioned in place relative to said arterial vessel, and pressed against a body surface of said subject so as to detect said pulse wave produced from said arterial vessel;
   a frame member for being set on said body surface of said subject;
   guide means supported by said frame member, for guiding said pulse wave sensor within a predetermined length along said cross line;
   a feeding screw supported by said frame member, said feeding screw being rotatable about a longitudinal axis thereof extending parallel to said cross line, said feeding screw being threadedly engaged with said pulse wave sensor;
   a drive motor supported by said frame member such that said drive motor is located adjacent to said body surface when said frame member is set on the body surface of said subject; and
   a transmission device provided between said drive motor and said feeding screw, said transmitting device transmitting rotating force of said drive motor to said feeding screw, so as to move said pulse wave sensor along said cross line.

2. The apparatus as set forth in claim 1, further comprising
   detecting means for detecting that said pulse wave sensor has been moved along said cross line to a middle point of said predetermined length.

3. The apparatus as set forth in claim 2, wherein said detecting means comprises
   a reflection plate mounted on said pulse wave sensor, and
   a photocoupler supported by said frame member, for emitting a light beam toward said reflection plate and detecting the light beam reflected by said reflection plate, said photocoupler generating an electric signal if an intensity of the received light beam exceeds a reference value, said electric signal representing that said pulse wave sensor has been moved to said middle point of said predetermined length.

4. The apparatus as set forth in claim 1, wherein said pulse wave sensor comprises:
   a movable member including a threaded portion with which said feeding screw is threadedly engaged,
   a diaphragm supported by said movable member, said diaphragm defining a fluid-tight space in said movable member,
   a presser member supported by said diaphragm, said presser member being movable relative to said movable member in a direction substantially perpendicular to the body surface of said subject as pressure in said fluid-tight space is varied, and
   a pressure detector secured to said presser member, for detecting said pulse wave produced from said arterial vessel of said subject and generating electric signal representing the detected pulse wave, said pressure detector being pressed against said body surface when said presser member is moved toward said body surface.

5. The apparatus as set forth in claim 1, wherein said guide means comprises
   a pair of parallel guide rails supported by said frame member.

6. The apparatus as set forth in claim 1, wherein said transmission device comprises
   a reduction-gear train consisting of a plurality of gears.

* * * * *